United States Patent [19]

Yoshida et al.

[11] 4,123,256
[45] Oct. 31, 1978

[54] N-(4-SUBSTITUTED BENZYLOXY)PHENYL)-N-METHYL-N-METHOXYUREA

[75] Inventors: Ryo Yoshida, Kawanishi; Ichiki Takemoto, Toyonaka; Seizo Sumida, Nishinomiya; Katsuzo Kamoshita, Osaka, all of Japan

[73] Assignee: Sumitomo Chemical Company, Limited, Osaka, Japan

[21] Appl. No.: 835,745

[22] Filed: Sep. 22, 1977

[30] Foreign Application Priority Data

Sep. 30, 1976 [JP] Japan .................. 51-118046

[51] Int. Cl.$^2$ .................. C07C 69/76; C07C 121/75; A01N 9/20
[52] U.S. Cl. .................. 71/105; 260/453 RW; 260/465 D; 71/120
[58] Field of Search .................. 260/453 RW, 465 D; 71/150, 120

[56] References Cited

U.S. PATENT DOCUMENTS

| 2,960,534 | 11/1960 | Scherer et al. | 260/453 AR |
| 3,431,289 | 3/1969 | Freund et al. | 260/453 RW |
| 3,819,697 | 6/1974 | Cross | 71/105 |

OTHER PUBLICATIONS

Merck Index, 8th Edition, Organic Name Reactions, p. 1226.

*Primary Examiner*—Lewis Gotts
*Assistant Examiner*—Robert C. Whittenbaugh
*Attorney, Agent, or Firm*—Birch, Stewart, Kolasch and Birch

[57] ABSTRACT

An N-[4-(substituted benzyloxy)phenyl]-N'-methyl-N'-methoxyurea of the formula:

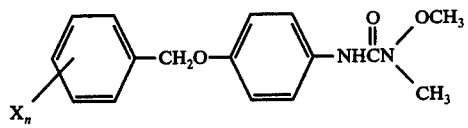

wherein X, which may be the same or different, is halogen, nitro, cyano, trifluoromethyl, lower alkyl or lower alkoxy and n is an integer of 1 to 5, which shows a pronounced herbicidal activity against a wide variety of weeds in the cultivation of soybean, kidney bean, peanut, cotton or rice plants without any material toxicity to mammals and said crop plants.

11 Claims, No Drawings

N-(4-SUBSTITUTED BENZYLOXY)PHENYL)-N-METHYL-N-METHOXYUREA

The present invention relates to N-[4-(substituted benzyloxy)phenyl]-N'-methyl-N'-methoxyureas of the formula:

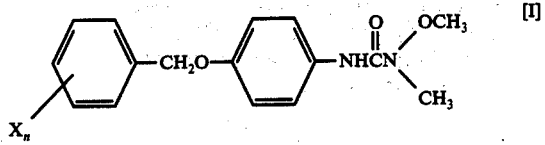

wherein X, which may be the same or different, is halogen (e.g., fluorine, chlorine, bromine), nitro, cyano, trifluoromethyl, lower alkyl (e.g., methyl, ethyl, propyl, butyl) or lower alkoxy (e.g., methoxy, ethoxy, propoxy) and n is an integer of 1 to 5, and their preparation and use.

Throughout this specification, the term "lower" used in connection with an alkyl group or an alkoxy group is intended to means those having not more than 8 carbon atoms, preferably not more than 4 carbon atoms for alkyl and not more than 3 carbon atoms for alkoxy.

As is well known, soybean, kidney bean, peanut, cotton, rice, etc. are crops of world-wide importance. The principal herbicides in the cultivation of the said crop plants now in use are of the soil-application type, and their application is made before emergence of weeds so that the period during which the herbicidal activity is maintained is limited to the early stage of the cultivation. Accordingly, a post-emergence herbicide which can be applied later to the foliar parts of weeds at their actively growing stages is desirable. But the fact is that the herbicides of this type now in practical use are limited in kind and, moreover, that those are frequently limited in application time and application method because of the phytotoxicity to the said crop plants. For example, chloroxuron (i.e., N-[4-(4-chlorophenoxy)-phenyl]-N',N'-dimethylurea) is in practical use as a selective foliar-applied herbicide in the cultivation of soybean plants, but it tends to exhibit a considerable phytotoxicity thereto at the primary to early trifoliate leaf stage by over-the-top post-emergence application and therefore has limitations as to its timing of application [Robert N. Anderson: Weed Science, 19, 219 (1971)].

It has now been found that the N-[4-(substituted benzyloxy)phenyl]-N'-methyl-N'-methoxyureas (hereinafter referred to as "substituted ureas") of the formula [I] exhibit a pronounced herbicidal activity against a wide variety of weeds, without damaging crop plants such as soybean, kidney bean, peanut, cotton and rice, by foliar-application. Since their selectivity to the said crop plants is highly remarkable, they can be safely applied to the area where such crop plants are cultivated and which is infested with various weeds by over-the-top foliar application to exterminate selectively the weeds. Furthermore, their toxicity to mammals is quite low and does not cause any injury thereto.

While the substituted ureas [I] are per se novel, there are some chemical-structurally related compounds known, examples of which are N-[4-(4-chlorobenzyloxy)-phenyl]-N',N'-dimethylurea, N-(3-chloro-4-benzyloxyphenyl)-N'-methyl-N'-methoxyurea and N-(4-phenoxyphenyl)-N'-methyl-N'-methoxyurea. Among them, however, the first one is described in U.S. Pat. No. 3,819,697 to have no selectivity to soybean, cotton, sugar beet, corn, etc. Further, the latter two, which are disclosed in Swiss Pat. No. 532,891, produce strong phytotoxicity against crop plants such as soybean and cotton as evidenced in Examples I and II hereinafter presented. Accordingly, the said finding is of unexpected nature.

The substituted ureas [I] of the present invention may be prepared by various methods, of which typical examples will be described below.

The first method comprises the reaction between a 4-(substituted benzyloxy)phenyl isocyanate [II] and N,O-dimethylhydroxylamine [III], which is representable by the formula:

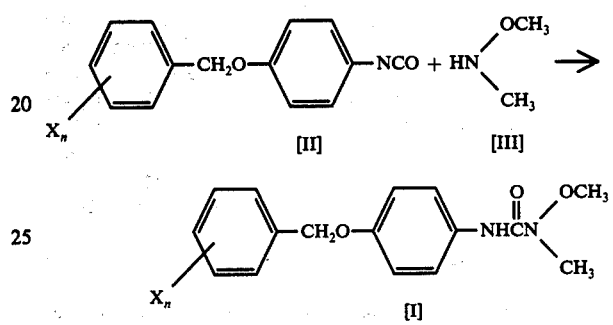

wherein X and n are each as defined above.

The reaction is usually carried out in an inert solvent (e.g., benzene, toluene, xylene) at a temperature from 10° to 100° C. For example, a solution of N,O-dimethylhydroxylamine [III] in benzene is added dropwise to a solution of the 4-(substituted benzyloxy)phenyl isocyanate [II] in benzene at room temperature, the amounts of the compounds [II] and [III] being equimolar. Thereafter, the mixture is stirred for 1 hour, and the solvent is then removed by evaporation to obtain the substituted urea [I].

The second method comprises the reaction between the 4-(substituted benzyloxy)phenyl isocyanate [II] and hydroxylamine [IV], followed by methylation of the resulting N-[4-(substituted benzyloxy)phenyl]-N'-hydroxyurea [V], which is representable by the formula:

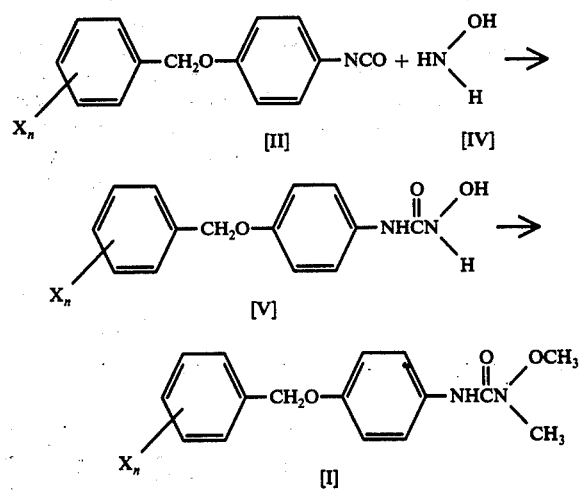

wherein X and n are each as defined above.

The reaction in the first step is normally carried out in an inert solvent (e.g., methylene chloride, chloroform) at a temperature from 0° to 30° C. The reaction in the second step is usually performed by treatment of the reaction product in the first step with a methylating agent (e.g., dimethyl sulfate, methyl iodide, diazomethane), preferably in an inert solvent (e.g., benzene, toluene, xylene, methanol, ethanol, tetrahydrofuran, dioxane, water) in the presence of a base (e.g., sodium hydroxide, potassium hydroxide) at a temperature from 10° to 100° C. For example, a solution of the 4-(substituted benzyloxy)phenyl isocyanate [II] in methylene chloride is added dropwise to an aqueous solution of hydroxylamine [IV] at room temperature, preferably below 20° C., the amounts of the compounds [II] and [IV] being equimolar. After stirring for 1 hour, the precipitated crystals are collected by filtration. The thus collected N-[4-(substituted benzyloxy)phenyl]-N'-hydroxyurea [V] is dissolved in a mixture of benzene and methanol, sodium hydroxide and dimethyl sulfate are added thereto, and then reaction is carried out at room temperature. The reaction mixture is extracted with benzene. The benzene extract is washed with water, and the solvent is evaporated to give the substituted urea [I].

The third method comprises the reaction between a 4-(substituted benzyloxy)aniline [VI] and an N-methoxy-N-methylcarbamyl halide [VII], which is representable by the formula:

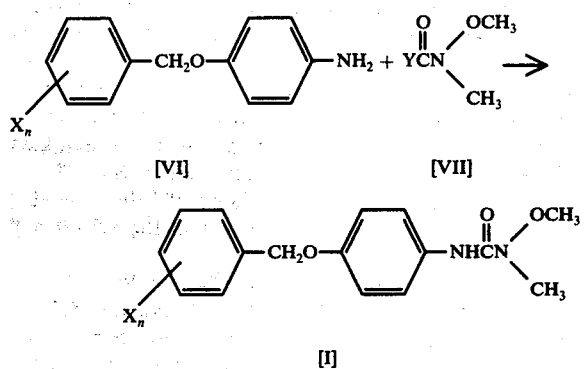

wherein Y is halogen (e.g., chlorine, bromine) and X and n are each as defined above.

Usually, the reaction is carried out in an inert solvent (e.g., benzene, toluene, xylene, tetrahydrofuran, chloroform, pyridine, N,N-dimethylformamide) at a temperature from 50° to 150° C. The presence of an acid-eliminating agent (e.g., pyridine, triethylamine, sodium hydroxide, potassium hydroxide, sodium carbonate) in the reaction system is generally preferred. For example, the 4-(substituted benzyloxy)aniline [VI] and the N-methoxy-N-methylcarbamyl halide [VII] in equimolar amounts are dissolved in toluene, a 50% aqueous sodium hydroxide solution is added thereto, and the resulting mixture is heated under reflux. Water is added to the reaction mixture to dissolve the by-produced sodium chloride, and the toluene layer is washed with water and the solvent is distilled out to give the substituted urea [I].

The fourth method comprises the reaction between a substituted benzyl halide [VIII] and N-(4-hydroxyphenyl)-N'-methyl-N'-methoxyurea [IX], which is representable by the formula:

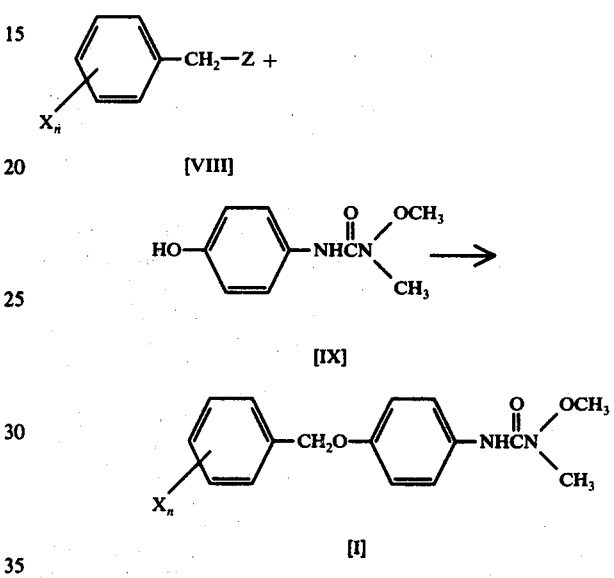

wherein Z is halogen (e.g., chlorine, bromine) and X and n are each as defined above.

Usually, the reaction is carried out in an inert solvent (e.g., benzene, toluene, xylene, tetrahydrofuran, methanol, ethanol, N,N-dimethylformamide) at a temperature from 50° to 100° C. The presence of an acid-eliminating agent (e.g., pyridine, triethylamine, sodium hydroxide, potassium hydroxide, sodium carbonate, sodium ethoxide) in the reaction system is generally desirable. For example, the substituted benzyl halide [VIII] is added to a solution of N-(4-hydroxyphenyl)-N'-methyl-N'-methoxyurea [IX] in benzene, and a 50% aqueous solution of sodium hydroxide is added thereto, the amounts of compounds [VIII] and [IX] and sodium hydroxide being equimolar. The mixture is heated under reflux and washed with water, followed by evaporation of the solvent to obtain the substituted urea [I].

Specific examples of the substituted urea [I] thus prepared are shown in Table 1.

Table 1

| Compound No. | $X_n$ | M.P. (° C) | Calcd. (%) C | H | N | Halogen | Found (%) C | H | N | Halogen |
|---|---|---|---|---|---|---|---|---|---|---|
| 1 | 2-F | 99–100 | 63.14 | 5.64 | 9.21 | | 63.05 | 5.56 | 9.10 | |
| 2 | 3-F | 104–105 | 63.14 | 5.64 | 9.21 | | 63.32 | 5.63 | 9.19 | |
| 3 | 4-F | 123–124.5 | 63.14 | 5.64 | 9.21 | | 63.11 | 5.54 | 9.31 | |
| 4 | 2-Cl | 98–99.5 | 59.91 | 5.34 | 8.73 | Cl: 11.05 | 59.84 | 5.20 | 8.72 | Cl: 11.04 |
| 5 | 4-Cl | 136–137 | 59.91 | 5.34 | 8.73 | Cl: 11.05 | 59.93 | 5.34 | 8.70 | Cl: 11.07 |

Table 1-continued

[Structure: phenyl ring with $X_n$ substituent — $CH_2O$ — phenyl — $NHC(=O)N(OCH_3)(CH_3)$]

| Compound No. | $X_n$ | M.P. (°C) | Calcd. (%) C | H | N | Halogen | Found (%) C | H | N | Halogen |
|---|---|---|---|---|---|---|---|---|---|---|
| 6 | 2-Br | 94–95 | 52.62 | 4.69 | 7.67 | Br: 21.88 | 52.46 | 4.72 | 7.76 | Br: 21.73 |
| 7 | 4-Br | 134–135 | 52.62 | 4.69 | 7.67 | Br: 21.88 | 52.58 | 4.69 | 7.63 | Br: 21.95 |
| 8 | 2,4-Cl$_2$ | 104–105 | 54.10 | 4.54 | 7.88 | Cl: 19.96 | 54.22 | 4.59 | 7.90 | Cl: 20.11 |
| 9 | 3,4-Cl$_2$ | 114–115 | 54.10 | 4.54 | 7.88 | Cl: 19.96 | 53.84 | 4.55 | 7.64 | Cl: 20.00 |
| 10 | 2,6-Cl$_2$ | 135–135.5 | 54.10 | 4.54 | 7.88 | Cl: 19.96 | 54.45 | 4.50 | 7.91 | Cl: 20.05 |
| 11 | 2,3,4,5,6-F$_5$ | 135–136 | 51.07 | 3.48 | 7.44 | | 50.91 | 3.48 | 7.36 | |
| 12 | 3-NO$_2$ | 124–125 | 58.00 | 5.17 | 12.68 | | 58.16 | 5.17 | 12.43 | |
| 13 | 4-NO$_2$ | 146–147.5 | 58.00 | 5.17 | 12.68 | | 58.20 | 5.29 | 12.48 | |
| 14 | 2-C≡N | 135–136 | 65.58 | 5.50 | 13.50 | | 65.76 | 5.68 | 13.64 | |
| 15 | 3-C≡N | 136–138 | 65.58 | 5.50 | 13.50 | | 65.63 | 5.51 | 13.58 | |
| 16 | 4-C≡N | 139–139.5 | 65.58 | 5.50 | 13.50 | | 65.32 | 5.71 | 13.44 | |
| 17 | 3-CH$_3$ | 88–89 | 67.98 | 6.71 | 9.33 | | 68.21 | 6.70 | 9.23 | |
| 18 | 4-CH$_3$ | 101–102 | 67.98 | 6.71 | 9.33 | | 68.00 | 6.86 | 9.14 | |
| 19 | 2,4-(CH$_3$)$_2$ | 86–87 | 68.77 | 7.05 | 8.91 | | 68.68 | 7.08 | 8.84 | |
| 20 | 3,4-(CH$_3$)$_2$ | 90–91 | 68.77 | 7.05 | 8.91 | | 68.80 | 7.01 | 8.90 | |
| 21 | 4-CH(CH$_3$)$_2$ | 87.5–88 | 69.49 | 7.37 | 8.53 | | 69.34 | 7.40 | 8.52 | |
| 22 | 4-C(CH$_3$)$_3$ | 124–125.5 | 70.15 | 7.65 | 8.18 | | 70.25 | 7.87 | 7.89 | |
| 23 | 2-OCH$_3$ | 98 | 64.53 | 6.38 | 8.85 | | 64.85 | 6.50 | 8.73 | |
| 24 | 4-OCH$_3$ | 110–113 | 64.53 | 6.38 | 8.85 | | 64.63 | 6.42 | 8.90 | |
| 25 | 2-OC$_3$H$_7$(iso) | 89–90 | 66.26 | 7.02 | 8.13 | | 66.37 | 7.02 | 8.08 | |
| 26 | 2-OCH$_3$, 5-Cl | 121–122 | 58.20 | 5.45 | 7.98 | Cl: 10.10 | 58.28 | 5.36 | 7.85 | Cl: 10.35 |
| 27 | 2-OCH$_3$, 3,5-Cl$_2$ | 81–82 | 53.00 | 4.71 | 7.27 | Cl: 18.41 | 53.23 | 4.90 | 7.18 | Cl: 18.27 |
| 28 | 2-CF$_3$ | 81–82 | 57.63 | 4.84 | 7.90 | | 57.41 | 4.82 | 7.83 | |
| 29 | 3-CF$_3$ | 93–94 | 57.63 | 4.84 | 7.90 | | 57.45 | 4.82 | 7.85 | |
| 30 | 3-Cl | 105–106 | 59.91 | 5.34 | 8.73 | Cl: 11.05 | 60.13 | 5.25 | 8.49 | Cl: 11.07 |

Practical embodiments of the preparation of the substituted ureas [I] are illustratively shown in the following examples.

EXAMPLE 1

To a solution of 4-(2-fluorobenzyloxy)phenyl isocyanate (24.3 g) in benzene (150 ml), a solution of N,O-dimethylhydroxylamine (20 g) in benzene (100 ml) is added dropwise at 20° to 30° C., and the resulting mixture is stirred at the same temperature for 30 minutes. The reaction mixture is concentrated in vacuo, and the residual crude crystals are recrystallized from ethanol to give N-[4-(2-fluorobenzyloxy)phenyl]-N'-methyl-N'-methoxyurea (Compound No. 1) (18 g) as white scales. M.P., 99° to 100° C.

Elementary analysis. Calcd. for C$_{16}$H$_{17}$N$_2$FO$_3$ (%): C, 63.14; H, 5.64; N, 9.21. Found (%): C, 63.05; H, 5.56; N, 9.10.

EXAMPLE 2

To a solution of 4-(4-fluorobenzyloxy)aniline (21.7 g) in benzene (150 ml), N-methyl-N-methoxycarbamyl chloride (14.7 g) and pyridine (11.8 g) are added thereto, and the reaction mixture is heated under reflux for 17 hours. The reaction mixture is cooled to room temperature, and water is added thereto to dissolve the by-produced pyridine hydrochloride. After separation of the aqueous layer, the benzene layer is washed with dilute hydrochloric acid and water in that order, dried and concentrated in vacuo to give N-[4-(4-fluorobenzyloxy)phenyl]-N'-methyl-N'-methoxyurea (Compound No. 3) (11 g) as white plates. M.P., 123° to 124.5° C.

Elementary analysis. Calcd. for C$_{16}$H$_{17}$N$_2$FO$_3$ (%): C, 63.14; H, 5.64; N, 9.21. Found (%): C, 63.11; H, 5.54; N, 9.31.

EXAMPLE 3

4-(3,4-Dichlorobenzyloxy)aniline (26.7 g), N-methoxy-N-methylcarbamyl chloride (13.5 g) and pyridine (8.7 g) are dissolved in toluene (200 ml), and the reaction mixture is heated under reflux for 5 hours. Water is added to the reaction mixture to dissolve the by-produced sodium chloride. The toluene layer is washed with dilute hydrochloric acid and water in that order, dried and concentrated under reduced pressure. The residual crude crystals are recrystallized from ethanol to give N-[4-(3,4-dichlorobenzyloxy)phenyl]-N'-methyl-N'-methoxyurea (Compound No. 9) (13 g) as white plates. M.P., 114° to 115° C.

Elementary analysis. Calcd. for C$_{16}$H$_{16}$N$_2$Cl$_2$O$_3$ (%): C, 54.10; H, 4.54; N, 7.88; Cl, 19.96. Found (%): C, 53.84; H, 4.55; N, 7.64; Cl, 20.00.

EXAMPLE 4

A solution of 4-(4-isopropylbenzyloxy)phenyl isocyanate (4.5 g) in methylene chloride (50 ml) is added dropwise to a solution of hydroxylamine hydrochloride (5.4 g) and sodium hydroxide (4 g) in water (15 ml) at a temperature below 20° C. The reaction mixture is diluted with water and filtered to give N-[4-(4-isopropylbenzoyloxy)-phenyl]-N'-hydroxyurea (4.1 g).

To a solution of the above obtained hydroxyurea (4.1 g) in a mixture of benzene and methanol (1:1 by volume) (200 ml), a 10 N aqueous sodium hydroxide solution (6 ml) and dimethyl sulfate (5 ml) are added dropwise alternatively below 30° C. The reaction mixture is stirred at room temperature and extracted with benzene. The benzene extract is concentrated under reduced pressure, and the residue is recrystallized from ethanol to give N-[4-(4-isopropylbenzyloxy)phenyl]-N'-methyl-N'-methoxyurea (2 g) (Compound No. 21) as white plates. M.P. 87.5° to 88.0° C.

Elementary analysis. Calcd. for $C_{19}H_{24}O_3N_2$ (%): C, 69.49; H, 7.37; N, 8.53. Found (%): C, 69.34; H, 7.40; N, 8.52.

EXAMPLE 5

To an ethanolic solution of sodium ethoxide prepared from ethanol (200 ml) and sodium (2.5 g), N-(4-hydroxyphenyl)-N'-methyl-N'-methoxyurea (20 g) is added, and a solution of 2-methoxybenzyl chloride (17 g) in N,N-dimethylformamide (50 ml) is added dropwise thereto. The reaction mixture is gradually heated, kept under reflux for 3 hours and cooled to room temperature. The reaction mixture is poured onto cold water (1 liter). The precipitated crystals are collected by filtration, washed with water, dried and recrystallized from ethanol to give N-[4-(2-methoxybenzyloxy)-phenyl]-N'-methyl-N'-methoxyurea (Compound No. 23) (12 g) as white scales. M.P., 98° C.

Elementary analysis. Calcd. for $C_{17}H_{20}N_2O_4$ (%): C, 64.53; H, 6.38; N, 8.85. Found (%): C, 64.85; H, 6.50; N, 8.73.

In the actual application as a herbicide, the substituted ureas [I] may be used alone without incorporation of any other ingredient such as a carrier or a diluent, but for easier application, are used in any of the ordinarily adopted forms such as, for example, dusts, wettable powders, oil sprays, aerosols, tablets, emulsifiable concentrates, granules and fine granules. In order to formulate these preparations, the substituted ureas [I] may be admixed with such solid carriers or diluents as mineral powders (e.g., talc, bentonite, montmorillonite, clay, kaolin, diatomaceous earth, mica, apatite, vermiculite, gypsum, calcium carbonate, slaked lime), plant powders (e.g., soybean, wheat, wood, tobacco, starch, crystalline cellulose), polymeric material powders (e.g., petroleum resin, polyvinyl chloride, dammar gum, ketonic resin), alumina or wax, or with such liquid carriers or diluents as alcohols (e.g., methanol, ethanol, ethylene glycol, benzyl alcohol), aromatic hydrocarbons (e.g., benzene, toluene, xylene, methylnaphthalene), chlorinated hydrocarbons (e.g., chloroform, carbon tetrachloride, monochlorobenzene), ethers (e.g., dioxane, tetrahydrofuran, ethylene glycol ethyl ether), ketones (e.g., acetone, methylethylketone, cyclohexanone), esters (e.g., ethyl acetate, butyl acetate, ethylene glycol acetate), acid amides (e.g., N,N-dimethylformamide) or nitriles (e.g., acetonitrile). If necessary, other additives such as gelatin, casein, sodium alginate, starch, agar or polyvinyl alcohol may be incorporated into the preparations. Further, the preparations may include extending agents as conventionally employed and/or other herbicides (e.g., diuron (i.e., N-(3,4-dichlorophenyl)-N',N'-dimethylurea), linuron (i.e., N-(3,4-dichlorophenyl)-N'-methoxy-N'-methylurea), chloroxuron (i.e., N-[4-(4-chlorophenoxy)phenyl]-N',N'-dimethylurea), 2,4-DB (i.e., 4-(2,4-dichlorophenoxy)butyric acid), fluometuron (i.e., N-(3-trifluoromethylphenyl)-N',N'-dimethylurea), dinoseb (i.e., 2,4-dinitro-6-sec.-butylphenol), bentazon (i.e., 3-isopropyl-1H-2,1,3-benzothiadiazin-4(3H)-one-2,2-dioxide)), microbial pesticides, pyrethroid type or other insecticides, fungicides, fertilizers, etc.

The concentration of the substituted ureas [I] as the active ingredient in the herbicidal composition is usually from about 2 to 80% by weight, although higher or lower concentrations may be employed.

Practical embodiments of the herbicidal composition according to the present invention are illustratively shown in the following examples, wherein parts and % are by weight.

EXAMPLE A

Preparation of wettable powder

Eighty parts of N-[4-(2-fluorobenzyloxy)phenyl]-N'-methyl-N'-methoxyurea (Compound No. 1), 5 parts of a wetting agent (alkylbenzenesulfonate type) and 15 parts of diatomaceous earth are well mixed while being powdered to obtain a wettable powder.

EXAMPLE B

Preparation of emulsifiable concentrate

Twenty parts of N-[4-(4-fluorobenzyloxy)phenyl]-N'-methyl-N'-methoxyurea (Compound No. 3), 30 parts of isophorone, 35 parts of xylene and 15 parts of polyoxyethylene phenyl ether are well mixed to obtain an emulsifiable concentrate.

EXAMPLE C

Preparation of dust

Two parts of N-[4-(3-methylbenzyloxy)phenyl]-N'-methyl-N'-methoxyurea (Compound No. 17) and 98 parts of clay are well mixed while being powdered to obtain a dust.

EXAMPLE D

Preparation of granules

Five parts of N-[4-(4-isopropylbenzyloxy)phenyl]-N'-methyl-N'-methoxyurea (Compound No. 21), 7 parts of lignin sulfonate and 88 parts of clay are well mixed while being powdered. The resultant mixture is admixed with water and granulated, followed by drying to give granules.

When the substituted ureas [I] are applied as a herbicide, the application method and the dosage rate depend upon the type of formulation of the active ingredient, the kinds of crop plants in cultivation, the kinds of weeds to be killed, the weather conditions, etc. It is preferably applied to both weeds and crop plants over the top in the post-emergence treatment, but it may be applied at any time ranging from the stage immediately after sowing. The dosage rate is generally about 2 to 80 grams, preferably 5 to 40 grams, of the active ingredient per are. For instance, the application to a cultivated land may be carried out to weeds of about 1 to 15 cm in height with a dose of about 2 to 80 grams per are by over-the-top foliar treatment. Further, for instance, the application to a paddy field may be carried out within 4 weeks after the transplantation of the seedlings of rice plants with a dose of the active ingredient in an amount of about 2 to 80 grams per are by water treatment.

As stated above, the substituted ureas [I] show a remarkable herbicidal activity against a wide variety of weeds. Examples of the weeds which can be exterminated are as follows: pigweed (*Amaranthus retroflexus*), common lambsquarter (*Chenopodium album*), cocklebur (*Xanthium pennsylvanicum*), morning glory (*Ipomoea purpurea*), chickweed (*Stellaria media*), bitter cress (*Cardamine flexuosa*), pale smartweed (*Polygonum aviculare*), large crabgrass (*Digitaria sanguinalis*) barnyard grass (*Echinochloa crus-galli*), green foxtail (*Setaria viridis*), nutsedge (*Cyperus difformis*), pickerelweed (*Monochoria vaginalis*), false pimpernel (*Lindernia pyxidaria*), toothcup (*Rotala indica*), radish (*Raphanus sativus*), etc.

The following examples show some typical test data indicating the excellent herbicidal activity of the substituted ureas [I]:

EXAMPLE I

Wagner pots (1/2000 are) were filled with upland soil, and the seeds of soybean, radish, pigweed, common lambsquarter, cocklebur, barnyard grass and large crabgrass were sowed in each of the pots and grown for 14 days in a greenhouse. The test compound formulated in a wettable powder preparation was diluted with water containing a wetting agent to give a spray volume of 3 liters/are. The test solution thus prepared was sprayed to the foliage of the test plants over the top by means of a small hand sprayer. At the time of the application, soybean was at the first trifoliate leaf stage, and the other plants were a the two-leaf stage. After spraying, the test plants were further grown for 20 days in the green-house to check the phytotoxicity and the herbicidal activity. Evaluation was made by the following standard:

| Rating value | Degree of phytotoxicity or herbicidal activity | Fresh weight (% of untreated) |
|---|---|---|
| 0 | No | 100 |
| 1 | Slight (plants recovered from damage) | 99 – 81 |
| 2 | Low | 80 – 51 |
| 3 | Moderate | 50 – 21 |
| 4 | High | 20 – 1 |
| 5 | Complete death | 0 |

The results are shown in Table 2.

Table 2

| Compound No. | Dosage rate (weight of active ingredient g/are) | Phytotoxicity Soybean | Herbicidal activity | | | | | |
|---|---|---|---|---|---|---|---|---|
| | | | Radish | Pigweed | Common lambs-quarter | Cocklebur | Barnyard grass | Large crab-grass |
| 1 | 20 | 0 | 5 | 5 | 5 | 5 | 5 | 5 |
| | 10 | 0 | 5 | 5 | 5 | 5 | 5 | 5 |
| | 5 | 0 | 5 | 5 | 5 | 5 | 5 | 3 |
| 2 | 20 | 0 | 5 | 5 | 5 | 5 | 4 | 5 |
| | 10 | 0 | 5 | 5 | 5 | 5 | 3 | 4 |
| 3 | 20 | 0 | 5 | 5 | 5 | 5 | 5 | 5 |
| | 10 | 0 | 5 | 5 | 5 | 5 | 5 | 5 |
| | 5 | 0 | 5 | 5 | 5 | 5 | 4 | 3 |
| 4 | 20 | 1 | 5 | 5 | 5 | 5 | 3 | 4 |
| | 10 | 0 | 5 | 5 | 5 | 5 | 2 | 2 |
| 5 | 20 | 1 | 5 | 5 | 5 | 5 | 5 | 5 |
| | 10 | 0 | 5 | 5 | 5 | 5 | 4 | 5 |
| 6 | 40 | 1 | 5 | 5 | 5 | 5 | 4 | 4 |
| | 20 | 0 | 5 | 5 | 5 | 5 | 2 | 4 |
| 9 | 20 | 2 | 5 | 5 | 5 | 5 | 3 | 5 |
| | 10 | 1 | 5 | 5 | 5 | 5 | 3 | 3 |
| 12 | 40 | 2 | 5 | 5 | 5 | 5 | 4 | 5 |
| | 20 | 0 | 5 | 5 | 5 | 5 | 2 | 3 |
| 15 | 40 | 0 | 5 | 5 | 5 | 5 | 3 | 3 |
| | 20 | 0 | 5 | 5 | 4 | 5 | 3 | 2 |
| 18 | 20 | 1 | 5 | 5 | 5 | 5 | 5 | 5 |
| | 10 | 1 | 5 | 5 | 5 | 5 | 5 | 5 |
| 19 | 40 | 1 | 5 | 5 | 5 | 5 | 4 | 4 |
| | 20 | 0 | 5 | 5 | 5 | 5 | 2 | 3 |
| 21 | 40 | 0 | 5 | 5 | 5 | 5 | 4 | 5 |
| | 20 | 0 | 5 | 5 | 5 | 5 | 4 | 4 |
| 22 | 20 | 1 | 5 | 5 | 5 | 5 | 4 | 5 |
| | 10 | 0 | 5 | 5 | 5 | 5 | 3 | 4 |
| 24 | 20 | 2 | 5 | 5 | 5 | 5 | 3 | 5 |
| | 10 | 1 | 5 | 5 | 5 | 5 | 3 | 3 |
| 27 | 20 | 1 | 5 | 5 | 5 | 5 | 4 | 4 |
| | 10 | 0 | 5 | 5 | 5 | 4 | 3 | 4 |
| 29 | 20 | 1 | 5 | 5 | 5 | 5 | 5 | 5 |
| | 10 | 1 | 5 | 5 | 5 | 5 | 4 | 5 |
| 30 | 20 | 0 | 5 | 5 | 5 | 5 | 4 | 4 |
| | 10 | 0 | 5 | 5 | 5 | 5 | 4 | 3 |
| Control (a) | 20 | 5 | 5 | 5 | 5 | 5 | 4 | 5 |
| | 10 | 4 | 5 | 5 | 5 | 5 | 4 | 3 |
| Control (b) | 20 | 5 | 5 | 5 | 5 | 5 | 5 | 5 |
| | 10 | 5 | 5 | 5 | 5 | 5 | 3 | 4 |
| Control (c) | 20 | 5 | 5 | 5 | 5 | 5 | 4 | 4 |
| | 10 | 4 | 5 | 5 | 5 | 3 | 2 | 4 |
| Control (d) | 20 | 3 | 5 | 5 | 5 | 5 | 4 | 3 |
| | 10 | 3 | 5 | 5 | 5 | 5 | 3 | 3 |

Note: Control (a), N-[4-(4-chlorobenzyloxy)phenyl]-N',N'-dimethylurea; Control (b), N-(3-chloro-4-benzyloxyphenyl)-N'-methyl-N'-methoxyurea; Control (c), N-(4-phenoxyphenyl)-N'-methyl-N'-methoxyurea; Control (d), chloroxuron.

EXAMPLE II

The test was carried out in the same manner as in Example I. Cotton, radish, pigweed, common lambsquarter, cocklebur and large crabgrass were used. Cotton was at the two-leaf stage when the application of the test compound was made. The results are shown in Table 3.

Table 3

| Compound No. | Dosage rate (weight of active ingredient g/are) | Phyto-toxicity Cotton | Herbicidal activity | | | | |
|---|---|---|---|---|---|---|---|
| | | | Radish | Pigweed | Common lambs-quarter | Cocklebur | Large crab-grass |
| 5 | 20 | 2 | 5 | 5 | 5 | 5 | 5 |

Table 3-continued

| Compound No. | Dosage rate (weight of active ingredient g/are) | Phytotoxicity Cotton | Herbicidal activity | | | | |
|---|---|---|---|---|---|---|---|
| | | | Radish | Pigweed | Common lambsquarter | Cocklebur | Large crabgrass |
| 6 | 10 | 1 | 5 | 5 | 5 | 5 | 5 |
| | 20 | 2 | 5 | 5 | 5 | 5 | 4 |
| 11 | 10 | 1 | 5 | 5 | 5 | 5 | 2 |
| | 20 | 1 | 5 | 5 | 5 | 5 | 4 |
| 13 | 10 | 0 | 5 | 5 | 5 | 5 | 4 |
| | 40 | 0 | 5 | 5 | 5 | 5 | 4 |
| 14 | 20 | 0 | 5 | 5 | 5 | 5 | 4 |
| | 40 | 1 | 5 | 5 | 5 | 5 | 3 |
| 16 | 20 | 0 | 5 | 5 | 5 | 5 | 3 |
| | 40 | 0 | 5 | 5 | 5 | 5 | 4 |
| 21 | 20 | 0 | 3 | 5 | 5 | 5 | 3 |
| | 10 | 2 | 5 | 5 | 5 | 5 | 5 |
| 25 | 20 | 0 | 5 | 5 | 5 | 5 | 4 |
| | 10 | 3 | 5 | 5 | 5 | 5 | 5 |
| 27 | 20 | 1 | 5 | 5 | 5 | 5 | 5 |
| | 10 | 0 | 5 | 5 | 5 | 5 | 5 |
| Control (a) | 20 | 0 | 5 | 5 | 5 | 5 | 4 |
| | 10 | 5 | 5 | 5 | 5 | 5 | 5 |
| Control (b) | 20 | 5 | 5 | 5 | 5 | 5 | 3 |
| | 10 | 5 | 5 | 5 | 5 | 5 | 5 |
| Control (c) | 20 | 5 | 5 | 5 | 5 | 5 | 4 |
| | 10 | 5 | 5 | 5 | 5 | 4 | 4 |

Note:
Control (a), N-[4-(4-chlorobenzyloxy)phenyl]-N'N'-dimethylurea; Control (b), N-(3-chloro-4-benzyloxyphenyl)-N'-methyl-N'-methoxyurea; Control (c) N-(4-phenoxyphenyl)-N'-methyl-N'-methoxyurea.

EXAMPLE III

Wagner's pots (1/5,000 are) were filled with paddy field soil and kept under paddy conditions. The seedlings of rice plants at the three-leaf stage were transplanted thereto, and the seeds of barnyard grass were sowed therein and cultured for 5 days. The test compound formulated in a wettable powder preparation was diluted with water and applied to the water layer at a volume of 15 ml per pot. Twenty-five days after the application, evaluation of phytotoxicity and herbicidal activity was made on rice plants and barnyard grass cultivated as well as nutsedge and broad-leaved weeds (e.g., pickerelweed, false pimpernel, toothcup) which emerged spontaneously. The standard of evaluation was the same as in Example I. The results are shown in Table 4.

Table 4

| Compound No. | Dosage rate (weight of active ingredient g/are) | Phytotoxicity Rice | Herbicidal activity | | |
|---|---|---|---|---|---|
| | | | Barnyard grass | Broadleaved weeds | Nutsedge |
| 1 | 20 | 0 | 5 | 5 | 5 |
| | 10 | 0 | 2 | 5 | 5 |
| 4 | 20 | 0 | 4 | 5 | 5 |
| | 10 | 0 | 2 | 5 | 5 |
| 7 | 20 | 0 | 3 | 5 | 5 |
| | 10 | 0 | 2 | 4 | 5 |
| 8 | 20 | 0 | 3 | 5 | 5 |
| | 10 | 0 | 3 | 5 | 5 |
| 10 | 40 | 0 | 3 | 5 | 5 |
| | 20 | 0 | 2 | 4 | 3 |
| 12 | 40 | 1 | 4 | 5 | 5 |
| | 20 | 0 | 2 | 5 | 5 |
| 13 | 40 | 0 | 4 | 5 | 5 |
| | 20 | 0 | 4 | 5 | 4 |
| 17 | 10 | 1 | 5 | 5 | 5 |
| | 5 | 0 | 4 | 5 | 5 |
| 19 | 20 | 0 | 5 | 5 | 5 |
| | 10 | 0 | 4 | 5 | 5 |
| 20 | 20 | 0 | 4 | 5 | 5 |
| | 10 | 0 | 4 | 5 | 5 |
| 22 | 20 | 0 | 4 | 5 | 5 |
| | 10 | 0 | 3 | 5 | 5 |
| 23 | 20 | 1 | 3 | 5 | 5 |
| | 10 | 0 | 3 | 5 | 5 |
| 26 | 20 | 0 | 4 | 5 | 5 |
| | 10 | 0 | 3 | 5 | 4 |
| 28 | 20 | 0 | 4 | 5 | 5 |
| Control (e) | 10 | 0 | 4 | 5 | 5 |
| | 10 | 3 | 4 | 5 | 5 |

Note:
Control (e), MCP (i.e., 2-methyl-4-chlorophenoxyacetic acid).

What is claimed is:

1. A compound of the formula:

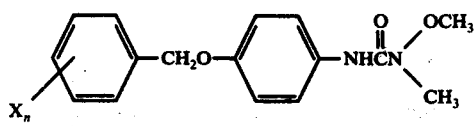

wherein X, which may be the same or different, is halogen, nitro, cyano, trifluoromethyl, lower alkyl or lower alkoxy and $n$ is an integer of 1 to 5.

2. The compound according to claim 1, wherein X, which may be the same or different, is halogen, nitro, cyano, lower alkyl or lower alkoxy and $n$ is an integer of 1 to 5.

3. The compound according to claim 1, wherein X, which may be the same or different, is fluorine, chlorine or bromine, nitro, cyano, trifluoromethyl, $C_1$-$C_4$ alkyl or $C_1$-$C_3$ alkoxy and $n$ is an integer of 1 to 5.

4. The compound according to claim 1, which has the formula:

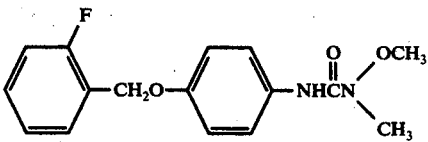

5. The compound according to claim 1, which has the formula:

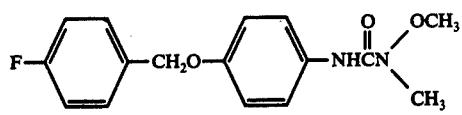

6. The compound according to claim 1, which has the formula:

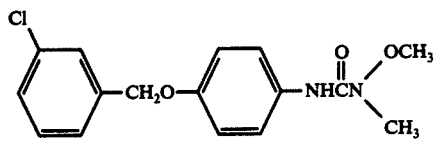

7. A method of selectively combating weeds in the cultivation of soybean, kidney bean, cotton, peanut or rice, which comprises applying a herbicidally effective amount of the compound according to claim 1 to the area wherein the soybean, kidney bean, cotton, peanut or rice crop is cultivated.

8. A herbicidal composition which comprises as an active ingredient a herbicidally effective amount of a compound of the formula:

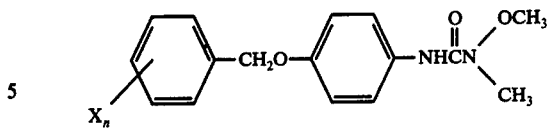

wherein X, which may be the same or different, is halogen, nitro, cyano, trifluoromethyl, lower alkyl or lower alkoxy and $n$ is an integer of 1 to 5, and an inert carrier.

9. The composition according to claim 8, wherein the concentration of the active ingredient is from about 2 to 80% by weight.

10. A herbicidal composition which comprises as an active ingredient a herbicidally effective amount of a compound of the formula:

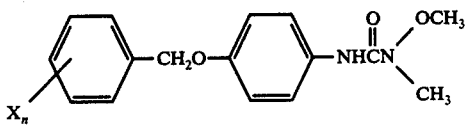

wherein X, which may be the same or different, is halogen, nitro, cyano, lower alkyl or lower alkoxy and $n$ is an integer of 1 to 5, and an inert carrier.

11. The composition according to claim 10, wherein the concentration of the active ingredient is from about 2 to 80% by weight.

* * * * *